US007238372B2

(12) United States Patent
Turkson et al.

(10) Patent No.: US 7,238,372 B2
(45) Date of Patent: Jul. 3, 2007

(54) METHODS FOR INHIBITING TUMOR CELL PROLIFERATION

(75) Inventors: James Turkson, Tampa, FL (US); Richard Jove, Tampa, FL (US); Jay W. Palmer, Sun City Center, FL (US); Heidi Kay, Wesley Chapel, FL (US); Hua Yu, Tampa, FL (US)

(73) Assignee: University of South Florida, Tampa, FL (US)

( * ) Notice: Subject to any disclaimer, the term of this patent is extended or adjusted under 35 U.S.C. 154(b) by 86 days.

(21) Appl. No.: 10/918,762

(22) Filed: Aug. 13, 2004

(65) Prior Publication Data

US 2005/0074502 A1  Apr. 7, 2005

Related U.S. Application Data

(60) Provisional application No. 60/525,295, filed on Nov. 25, 2003, provisional application No. 60/519,943, filed on Nov. 14, 2003, provisional application No. 60/515,580, filed on Oct. 30, 2003, provisional application No. 60/481,226, filed on Aug. 13, 2003.

(51) Int. Cl.
*A61K 33/24* (2006.01)
*C07F 15/00* (2006.01)

(52) U.S. Cl. .................. 424/649; 424/469; 556/137

(58) Field of Classification Search ............... 424/649; 514/492; 556/137
See application file for complete search history.

(56) References Cited

U.S. PATENT DOCUMENTS

| | | | | |
|---|---|---|---|---|
| 5,849,790 | A | * | 12/1998 | Palmer et al. ............... 514/492 |
| 6,511,676 | B1 | * | 1/2003 | Boulikas ..................... 424/450 |
| 2002/0035243 | A1 | | 3/2002 | Imfeld et al. |
| 2002/0120100 | A1 | | 8/2002 | Bonny |
| 2003/0032594 | A1 | | 2/2003 | Bonny |

OTHER PUBLICATIONS

Tukson et al. (Oncogene 2000: 19; 6613-6626).*
Zheligovskaya et al. Vestnik Moskovskogo Universiteta. Khimiya, 1970, pp. 32-37, vol. 11, No. 1, XP009041901.
U.S. Appl. No. 10/918,769, Kay et al.
U.S. Appl. No. 11/030,567, Kay et al.
Akira, S. "Roles of STAT3 Defined by Tissue-Specific Gene Targeting", *Oncogene*, 2000, pp. 2607-2611, vol. 19.
Ardizzoni, A. et al., "The Combination of Etoposide and Cisplatin in Non-Small-Cell Lung Cancer (NSCLC)", *Ann. Oncol.*, 1999, pp. S13-17, vol. 10.
Bowman, T. et al. "STATs in Oncogenesis", *Oncogene*, 2000, pp. 2474-2488, vol. 19.
Bowman, T. et al. "Stat3-Mediated Myc Expression is Required for Src Transformation and PDGF-Induced Mitogenesis", *Proc Natl. Acad. Sci. USA*, 2000, pp. 7319-7324, vol. 98, No. 3.

Bromberg, J. F. et al. "Transcriptionally Active Stat1 is Required for the Antiproliferative Effects of Both Interferon Alpha and Interferon Gamma", *Proc. Natl. Acad. Sci. USA*, 1996, pp. 7673-7678, vol. 93.
Bromberg, J. F. et al. "Stat3 Activation is Required for Cellular Transformation by V-src", *Mol. Cell. Biol.*, 1998, pp. 2553-2558, vol. 18, No. 5.
Bromberg, J. F. et al. "Stat3 as an Oncogene", *Cell*, 1999, pp. 295-303, vol. 98.
Catlett-Falcone, R. et al. "Constitutive Activation of Stat3 Signaling Confers Resistance to Apoptosis in Human U266 Myeloma Cells", *Immunity*, 1999, pp. 105-115, vol. 10.
Catlett-Falcone, R. et al. "STAT Proteins as Novel Targets for Cancer Therapy", *Curr. Opin. Oncol.*, 1999, pp. 490-496, vol. 11.
Coffer, P. J. et al. "The Role of STATs in Myeloid Differentiation and Leukemia", *Oncogene*, 2000, pp. 2511-2522, vol. 19.
Darnell, J. E., Jr. et al. "Jak-STAT Pathways and Transcriptional Activation in Response to IFNs and Other Extracellular Signaling Proteins", *Science*, 1994, pp. 1415-1421, vol. 264, No. 5164.
Darnell, J. E., Jr. "STATs and Gene Regulation", *Science*, 1997, pp. 1630-1635, vol. 277.
Epling-Burnette, P. K. et al. "Inhibition of STAT3 Signaling Leads to Apoptosis of Leukemic Large Granular Lymphocytes and Decreased Mcl-1 Expression", *J. Clin. Invest*, 2001, pp. 351-361, vol. 107, No. 3.
Fukada, T. et al. "Two Signals are Necessary for Cell Proliferation Induced by a Cytokine Receptor gp130: Involvement of STAT3 in Anti-Apoptosis", *Immunity*, 1996, pp. 449-460, vol. 5.
Garcia, R. et al. "Constitutive Activation of Stat3 in Fibroblasts Transformed by Diverse Oncoproteins and in Breast Carcinoma Cells", *Cell Growth Diff.*, 1997, pp. 1267-1276, vol. 8.
Garcia, R. et al. "Activation of STAT Transcription Factors in Oncogenic Tyrosine Kinase Signaling", *J. Biomed. Sci.*, 1998, pp. 79-85, vol. 5.
Garcia, R. et al. "Constitutive Activation of Stat3 by the Src and JAK Tyrosine Kinases Participates in Growth Regulation of Human Breast Carcinoma Cells", *Oncogene*, 2001, pp. 2499-2513, vol. 20.
Gouilleux, F. et al. "Prolactin and Interleukin-2 Receptors in T Lymphocytes Signal Through A MGF-STAT5-like Transcription Factor", *Endocrinology*, 1995, pp. 5700-5708, vol. 136, No. 12.
Grandis, J. R. et al. "Requirement of Stat3 but Not Stat1 Activation for Epidermal Growth Factor Receptor-Mediated Cell Growth In Vitro", *J. Clin. Invest.*, 1998, pp. 1385-1392, vol. 102, No. 7.
Grandis, J. R. et al. "Constitutive Activation of Stat3 Signaling Abrogates Apoptosis in Squamous Cell Carcinogenesis In Vivo", *Proc. Natl. Acad. Sci. USA*, 2000, pp. 4227-4232, vol. 97, No. 8.
Grandis, J. R. et al. "Epidermal Growth Factor Receptor—Mediated Stat3 Signaling Blocks Apoptosis in Head and Neck Cancer", *Laryngoscope*, 2000, pp. 868-874, vol. 110.
Hirano, T. et al. "Roles of STAT3 in Mediating the Cell Growth, Differentiation and Survival Signals Relayed Through the IL-6 Family of Cytokine Receptors", *Oncogene*, 2000, pp. 2548-2556, vol. 19.

(Continued)

*Primary Examiner*—Shanon Foley
*Assistant Examiner*—Brandon Fetterolf
(74) *Attorney, Agent, or Firm*—Saliwanchik, Lloyd & Saliwanchik

(57) ABSTRACT

The subject invention concerns methods for inhibition of STAT biological functions using platinum complexes.

4 Claims, 8 Drawing Sheets
(1 of 8 Drawing Sheet(s) Filed in Color)

OTHER PUBLICATIONS

Horiguchi, A. et al. "STAT3, but Not ERKs, Mediates the IL-6-Induced Proliferation of Renal Cancer Cells, ACHN and 769P", *Kidney Int*, 2002, pp. 926-938, vol. 61.

Johnson, P. J. et al. "Overexpressed pp60$^{c-src}$ Can Induce Focus Formation Without Complete Transformation of NIH 3T3 Cells", *Mol. Cell. Biol.*, 1985, pp. 1073-1083, vol. 5, No. 5.

Kotenko, S. V. et al. "Jak-Stat Signal Transduction Pathway Through the Eyes of Cytokine Class II Receptor Complexes", *Oncogene*, 2000, pp. 2557-2565, vol. 19.

Kunisada, K. et al. "Activation of gp130 Transduces Hypertrophic Signals Via STAT3 in Cardiac Myocytes", *Circulation*, 1998, pp. 346-352, vol. 98.

Lin, T. S. et al. "STAT Signaling in the Pathogenesis and Treatment of Leukemias", *Oncogene*, 2000, pp. 2496-2504, vol. 19.

Nielsen, M. et al. "Constitutive Activation of a Slowly Migrating Isoform of Stat3 in Mycosis Fungoides: Tyrphostin AG490 Inhibits Stat3 Activation and Growth of Mycosis Fungoides Tumor Cell Lines", *Proc. Natl. Acad. Sci. USA*, 1997, pp. 6764-6769, vol. 94.

Nielsen, M. et al. "Inhibition of Constitutively Activated Stat3 Correlates with Altered Bcl-2/Bax Expression and Induction of Apoptosis in Mycosis Fungoides Tumor Cells", *Leukemia*, 1999, pp. 735-738, vol. 13.

Nitiss, J. L. "A Copper Connection to the Uptake of Platinum Anticancer Drugs", *Proc. Natl. Acad. Sci. USA*, 2002, pp. 13963-13965, vol. 99, No. 22.

Persons, D. L. et al. "Cisplatin-Induced Activation of Mitogen-Activated Protein Kinases in Ovarian Carcinoma Cells: Inhibition of Extracellular Signal-Regulated Kinase Activity Increases Sensitivity to Cisplatin", *Clin. Cancer Res.*, 1999, pp. 1007-1014, vol. 5.

Sanchez-Perez, I. et al. "Cisplatin Induces a Persistent Activation of JNK That is Related to Cell Death", *Oncogene*, 1998, pp. 533-540, vol. 16.

Schindler, C. et al. "Transcriptional Responses to Polypeptide Ligands: The JAK-STAT Pathway", *Annu. Rev. Biochem.*, 1995, pp. 621-651, vol. 64.

Seidel, H. M. et al. "Spacing of Palindromic Half Sites as a Determinant of Selective STAT (Signal Transducers and Activators of Transcription) DNA Binding and Transcriptional Activity", *Proc. Natl. Acad. Sci. USA*, 1995, pp. 3041-3045, vol. 92.

Smithgall, T. E. et al. "Control of Myeloid Differentiation and Survival by Stats", *Oncogene*, 2000, pp. 2612-2618, vol. 19.

Song, J. I. et al. "STAT Signaling in Head and Neck Cancer", *Oncogene*, 2000, pp. 2489-2495, vol. 19.

Stark, G. R. et al. "How Cells Respond to Interferons", *Annu. Rev. Biochem*, 1998, pp. 227-264, vol. 67.

Turkson, J. et al. "Stat3 Activation by Src Induces Specific Gene Regulation and is Required for Cell Transformation", *Mol. Cell. Biol.*, 1998, pp. 2545-2552, vol. 18, No. 5.

Turkson, J. et al. "Requirement for Ras/Rac1-Mediated p38 and c-Jun N-Terminal Kianse Signaling in Stat3 Transcriptional Activity Induced by the Src Oncoprotein", *Mol. Cell. Biol.*, 1999, pp. 7519-7528, vol. 19, No. 11.

Turkson, J. et al. "STAT Proteins: Novel Molecular Targets for Cancer Drug Discovery", *Oncogene*, 2000, pp. 6613-6626, vol. 19.

Turkson, J. et al. "Phosphotyrosyl Peptides Block Stat3-Mediated DNA Binding Activity, Gene Regulation, and Cell Transformation", *J. Biol. Chem.*, 2001, pp. 45443-45455, vol. 276, No. 48.

Wagner, B. J. et al. "The SIF Binding Element Confers sis/PDGF Inducibility Onto the c-fos Promoter", *EMBO J.*, 1990, pp. 4477-4484, vol. 9, No. 13.

Yu, C. L. et al. "Enhanced DNA-Binding Activity of a Stat3-Related Protein in Cells Transformed by the Src Oncoprotein", *Science*, 1995, pp. 81-83, vol. 269, No. 32.

Zhang, Y. et al. "Activation of Stat3 in v-Src-Transformed Fibroblasts Requires Cooperation of Jak1 Kinase Activity", *J. Biol. Chem.*, 2000, pp. 24935-24944, vol. 275.

Cuny, G.D. et al. "Photoactivated Virucidal Properties of Tridentate 2,2'-Dihydroxy Azobenzene and 2-Salicylideneaminophenol Platinum Pyridine Complexes", *Bioorganic & Medicinal Chemistry Letters*, 1999, pp. 237-240, vol. 9.

Toyoizumi, T. et al. "Combined Therapy with Chemotherapeutic Agents and Herpes Simplex Virus Type 1 ICP34.5 Mutant (HSV-1716) in Human Non-Small Cell Lung Cancer", 1999, *Human Gene Therapy*, pp. 3013-3029, vol. 10.

\* cited by examiner

FIG. 5A
FIG. 5B
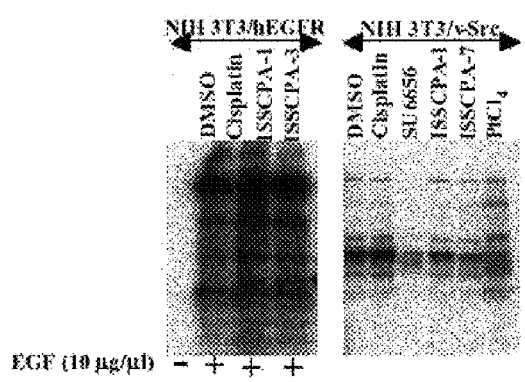
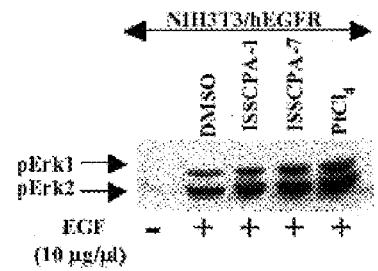
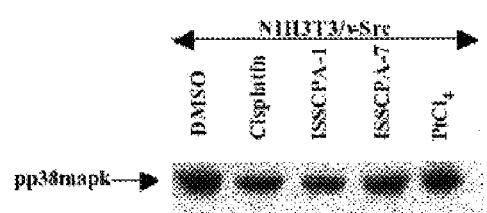
FIG. 5C

FIG. 8A
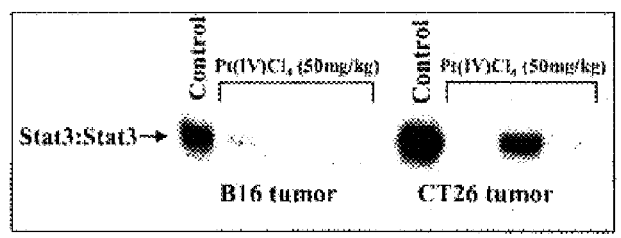
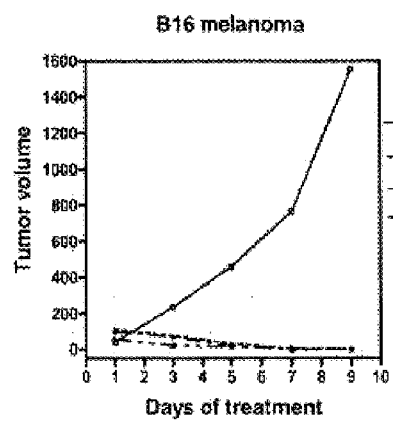
FIG. 8B
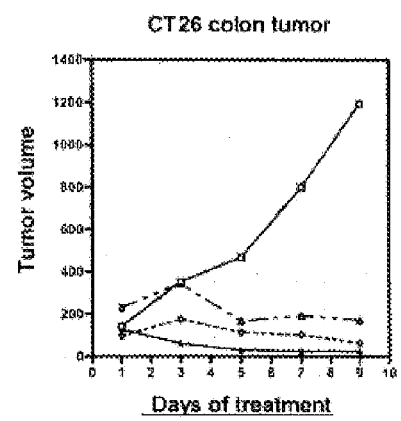
FIG. 8C

SEQUENCE LISTING

<160> NUMBER OF SEQ ID NOS: 3

<210> SEQ ID NO 1
<211> LENGTH: 24
<212> TYPE: DNA
<213> ORGANISM: Artificial sequence
<220> FEATURE:
<223> OTHER INFORMATION: oligonucleotide probe

<400> SEQUENCE: 1
agcttcattt cccgtaaatc ccta                                          24

<210> SEQ ID NO 2
<211> LENGTH: 18
<212> TYPE: DNA
<213> ORGANISM: Artificial sequence
<220> FEATURE:
<223> OTHER INFORMATION: oligonucleotide probe

<400> SEQUENCE: 2
agatttctag gaattcaa                                                 18

<210> SEQ ID NO 3
<211> LENGTH: 26
<212> TYPE: DNA
<213> ORGANISM: Artificial sequence
<220> FEATURE:
<223> OTHER INFORMATION: oligonucleotide probe

<400> SEQUENCE: 3
tcgacagagg ggactttccg agaggc                                        26

US 7,238,372 B2

METHODS FOR INHIBITING TUMOR CELL PROLIFERATION

CROSS-REFERENCE TO RELATED APPLICATIONS

This application claims the benefit of U.S. Provisional Application Ser. No. 60/481,226, filed Aug. 13, 2003, U.S. Provisional Application Ser. No. 60/515,580, filed Oct. 30, 2003, and U.S. Provisional Application Ser. No. 60/525,295, filed Nov. 25, 2003, and U.S. Provisional Application Ser. No. 60/519,943, filed Nov. 14, 2003, the disclosure of each of which is incorporated herein by reference in its entirety.

This invention was made with government support under National Cancer Institute grant number 5 P01 CA78038-03. The government has certain rights in the invention.

BACKGROUND OF THE INVENTION

Cellular responses to growth factors and cytokines are characterized by activation of the Signal Transducer and Activator of Transcription (STAT) family of cytoplasmic transcription factors (Darnell, 1997; Darnell et al., 1994; Schindler et al., 1995; Stark et al., 1998; Smithgall et al., 2000; Akira, 2000; Hirano et al., 2000; Bromberg et al., 1996; Fukada et al., 1996; Kotenko et al., 2000). STATs are activated at a very early stage in the transduction pathway by tyrosine phosphorylation that is induced by protein tyrosine kinases of growth factor receptors, receptor-associated Janus kinase (Jaks) or Src kinase families. This in turn induces phosphotyrosine (pTyr)-SH2 interactions between two STAT monomers and the formation of dimers, which then translocate to the nucleus, bind to specific DNA response elements and regulate the expression of genes essential for cell proliferation, differentiation, development and survival.

Normal STAT activation is tightly-regulated and has a short duration, which is in keeping with normal cellular requirements for mounting a response to external stimuli. However, persistent activation of specific STAT proteins, particularly Stat3 and Stat5, occurs with high frequency in some tumors, and persistently-active Stat3 has a causal role in malignant transformation by promoting growth and survival of transformed and tumor cells, including those breast, prostate and head and neck squamous carcinoma cells, lymphomas and leukemias (Bromberg et al., 1999; Turkson et al., 1998; Bromberg et al., 1998; Catlett-Falcone et al., 1999a; Garcia et al., 2001; Grandis et al., 2000a; Grandis et al., 1998; Nielsen et al., 1997; Nielsen et al., 1999; Epling-Burnette et al., 2001; reviewed in Bowman et al., 2000a; Turkson et al., 2000; Song et al., 2000; Coffer et al., 2000; Lin et al., 2000; Catlett-Falcone et al., 1999b; Garcia et al., 1998). Of clinical importance, blockade of Stat3 signaling in malignant cells or whole tumors that contain persistently-active Stat3 induces apoptosis and tumor regression.

Platinum complexes, the prototype of cisplatin, have been widely used as active anticancer agents (Ardizzoni et al., 1999; Nitiss, 2002) in a variety of human tumors, including testicular, ovarian, bladder carcinoma, head and neck, and non-small cell lung cancers. The outcome of treatments with cisplatin and other platinum-containing compounds is strongly linked to their alkylating effects on DNA. However, the potential impact of platinum-complex-based therapy on cellular signaling and the therapeutic importance of such interactions have yet to be explored. Reports show that cisplatin induces activation of members of the mitogen-activated protein kinase (MAPK) pathways (Persons et al., 1999; Sanchez-Perez et al., 1998), which may influence drug-induced apoptosis.

BRIEF SUMMARY OF THE INVENTION

The subject invention concerns methods for inhibiting STAT protein function using platinum complexes. In one embodiment, a platinum complex is contacted with a cell expressing a STAT protein. The STAT protein can be, for example, stat3.

BRIEF DESCRIPTION OF THE FIGURES

The patent or application file contains at least one drawing executed in color. Copies of this patent or patent application publication with color drawings will be provided by the Patent Office upon request and payment of the necessary fee.

FIG. 1A shows Stat1 and Stat3 binding activities to hSIE probe, FIG. 1B shows Stat1 and Stat5 binding activities to MGFe probe, FIG. 1C shows the binding of E2F1 to DHFR sequence as probe, and FIG. 1D shows the binding of NFκB to binding sequence in alpha-2 macroglobulin promoter as probe. Positions of complexes of DNA with STAT, E2F1 or NFκB (p65, p50) in gel are labeled. Control lanes represent nuclear extracts that are not pre-incubated with platinum complexes.

FIGS. 5A–C are photographs showing the effects of platinum complexes on signal molecules. Fibroblasts over-expressing EGF receptor (NIH3T3/Hegfr) and their v-Src-transformed counterparts (NIH3T3/v-Src) were treated with platinum complexes for 24 h and stimulated with or without EGF for 5 min. Whole cell lysates were prepared and analyzed on 5% SDSPAGE and transferred to a nitrocellulose membrane and probed by Western blotting using (Panel A) anti-pTyr antibody (4G10) or antibodies against activated forms of the members of the MAPK family, (Panel B) ERKs, and (Panel C) p38mapk.

FIG. 6A shows normal or v-Src-transformed mouse fibroblasts in culture treated with platinum complexes for the indicated times and number of viable cells enumerated by visualization under microscope and trypan blue exclusion. FIG. 6B shows normal and Src-transformed mouse fibroblasts, human breast epithelial as well as tumor cells of the breast (MDA-MB-231, MDA-MB-435, MDA-MB-453, and MCF-7), lung (A549) and prostate (DU145) treated with or without platinum complexes for 24–48 hrs and analyzed for extent of [$^3$H] thymidine incorporation. Values are the mean and S.D. of 3–4 independent determinations.

FIGS. 8A–C show tumor regression induced by platinum (IV) chloride. Tumor models in mice using B16 melanoma and CT26 colon tumors both of which harbor constitutively-active Stat3 were treated by intra-tumoral injection with doses of platinum (IV) chloride and tumor sizes monitored every other day for up to 9 days. FIG. 8A is a photograph showing extracted tumor tissues were analyzed for Stat3 activity in in vitro DNA-binding assays and EMSA analysis. FIG. 8B and FIG. 8C show tumor sizes monitored by calipers plotted against days of treatment.

BRIEF DESCRIPTION OF THE SEQUENCES

Figure 1A:
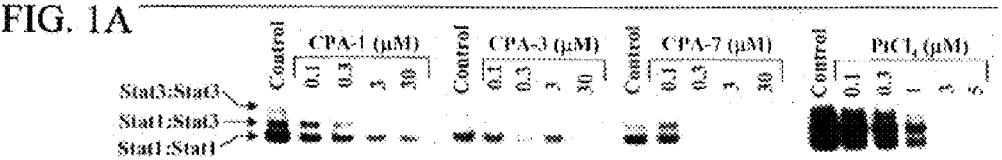
FIGS. 1A–D are photographs showing EMSA analyses of DNA-binding activities and effects of platinum complexes. Nuclear extracts containing activated Stat1, Stat3 and Stat5 are treated with the indicated concentrations of platinum complex ISSCPA-1, ISSCPA-3, ISSCPA-7, or $PtCl_4$ for 30 min at room temperature prior to incubation with radiolabeled oligonucleotide probes.

SEQ ID NO:1 is the nucleotide sequence of an oligonucleotide probe.

SEQ ID NO:2 is the nucleotide sequence of an oligonucleotide probe.

SEQ ID NO:3 is the nucleotide sequence of an oligonucleotide probe.

DETAILED DISCLOSURE OF THE INVENTION

The subject invention concerns methods for inhibiting function of STAT proteins. Platinum complexes useful in the subject invention are shown below:

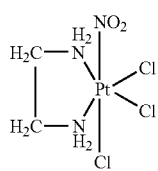

CPA-1

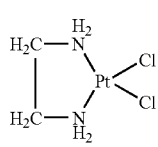

CPA-3

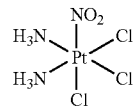

CPA-7

The subject platinum complexes can be prepared using standard chemical synthesis methods and materials known in the art.

Compounds of the subject invention also include pharmaceutically-acceptable salts of the subject platinum complexes. The term pharmaceutically-acceptable salts means salts of the platinum complexes of the invention which are prepared with acids or bases, depending on the particular substituents found on the subject complexes described herein. Examples of a pharmaceutically-acceptable base addition salts include sodium, potassium, calcium, ammonium, or magnesium salt. Examples of pharmaceutically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically-acceptable salts of platinum complexes of the invention can be prepared using conventional techniques.

It will be appreciated by those skilled in the art that certain of the platinum complexes of the invention may contain one or more asymmetrically substituted carbon atoms which can give rise to stereoisomers. It is understood that the invention extends to all such stereoisomers, including enantiomers, and diastereoisomers and mixtures, including racemic mixtures thereof.

The platinum complexes of the subject invention are potent and selective disruptors of STAT activity. Exemplified compounds ISSCPA-1 (also designated herein as CPA-1) and ISSCPA-7 (also designated herein as CPA-7) strongly disrupt Stat3 activity and interfere with its ability to bind to its consensus binding sequence. The platinum complexes of the invention induce cell growth inhibition and apoptosis in transformed cells and tumor cells with persistently active STATs. Malignant cells with aberrant or constitutive STAT signaling are highly sensitive to platinum complexes of the invention. General cytotoxicity of the subject platinum complexes to normal cells is minimal or nil. The observation that the exemplified compounds ISSCPA-1 and ISSCPA-7 selectively block the growth and replication of transformed and tumor cells that contain abnormal Stat3 activity while only slowing the growth of cells that do not have abnormal Stat3 activity is highly significant. In addition, strong apoptosis is induced by platinum compounds of the invention in malignant cells that harbor persistently-active STAT signaling, which correlates with suppression of aberrant STAT activity in these cells.

Platinum complexes of the subject invention also exhibit anti-tumor activity in melanoma and colon tumors in vivo. The abrogation of constitutively-active STATs in tumors treated with platinum complexes of the invention is consistent with their effects on STAT activity both in vitro and in whole cells, and together establish STAT-based anti-tumor effects of these compounds.

Methods of the invention comprise inhibiting function of a STAT by contacting a cell expressing a STAT with a platinum complex of the invention wherein the complex is taken in or otherwise provided inside the cell. In an exemplified embodiment, platinum complexes ISSCPA-1 and ISSCPA-7 physically interact with the DNA-binding domain of Stat3 and thereby disrupts its ability to bind to DNA. In Src-transformed mouse fibroblasts, as well as in human tumor cells of the breast, prostate, and lung, and mouse melanoma cells that contain constitutive Stat3 activity, both ISSCPA-1 and ISSCPA-7 abrogate Stat3 signaling function and thereby induce cell growth inhibition and apoptosis.

Methods of the invention also comprise inhibiting the function and/or growth and replication of a cell that is aberrantly or constitutively expressing a STAT, such as Stat1 or Stat3. In one embodiment, the method comprises contacting a cell with a platinum complex of the invention. In one embodiment, the cell is a tumor cell, cancer cell, or a transformed cell. The cell can be a cell from a mammal, including human, monkey, chimpanzee, ape, dog, cat, horse, cow, or pig. Platinum complexes of the invention can be delivered to a cell either through direct contact with the cell or via a carrier means. Carrier means for delivering compositions to cells are known in the art and include, for example, encapsulating the platinum complex in a liposome moiety. Another means for delivery of a platinum complex of the invention to a cell comprises attaching the platinum complexes to a protein or nucleic acid that is targeted for delivery to the target cell. Published U.S. patent application Ser. Nos. 20030032594 and 20020120100 disclose amino acid sequences that can be coupled to another composition and that allows the composition to be translocated across biological membranes. Published U.S. patent application Ser. No. 20020035243 also describes compositions for transporting biological moieties across cell membranes for intracellular delivery.

Therapeutic application of the subject platinum complexes, and compositions containing them, can be accomplished by any suitable therapeutic method and technique presently or prospectively known to those skilled in the art. The subject platinum complexes can be administered by any suitable route known in the art including, for example, oral, nasal, rectal, and parenteral routes of administration. As used herein, the term parenteral includes subcutaneous, introdermal, intravenous, intramuscular, intraperitoneal, and intrasternal administration, such as by injection. Administration of the subject platinum complexes of the invention can be continuous or at distinct intervals as can be readily determined by a person skilled in the art. An ordinarily skilled clinician can determine an amount of a platinum complex of the invention to be administered to a patient that will be effective to treat the particular condition, disease, or disorder of the patient.

Compounds useful in the methods of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive platinum complex is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject platinum complexes include ethanol, dimethyl sulfoxide, glycerol, alumina, starch, and equivalent carriers and diluents. To provide for the administration of such dosages for the desired therapeutic treatment, pharmaceutical compositions of the invention will advantageously comprise between about 0.1% and 99%, and especially, 1 and 15% by weight of the total of one or more of the subject platinum complexes based on the weight of the total composition including carrier or diluent.

The compounds of the subject invention can also be administered utilizing liposome technology, slow release capsules, implantable pumps, and biodegradable containers. These delivery methods can, advantageously, provide a uniform dosage over an extended period of time. The platinum complexes of the invention can also be administered in their salt derivative forms or cystalline forms.

All patents, patent applications, provisional applications, and publications referred to or cited herein are incorporated by reference in their entirety, including all figures and tables, to the extent they are not inconsistent with the explicit teachings of this specification.

MATERIALS AND METHODS

Cells, plasmids, and other reagents.

v-Src-transformed (NIH3T3/v-Src) and derived counterparts stably expressing Stat3 reporter, pLucTKS3 (NIH3T3/v-Src/pLucTKS3) or Stat3-independent plasmid, pRLSRE (NIH3T3/v-Src/pRLSRE), and Ras-transformed (NIH3T3/v-Ras) fibroblasts, human breast carcinoma MDA-MB-231, MDA-MB-435, MDA-MB-453 and MDA-MB-468, melanoma B16 cells, prostate cancer cells, DU145 and PC3, as well as human lung carcinoma A459 cells have been previously described (Garcia et al., 2001; Turkson et al., 2001; Yu et al., 1995; Johnson et al., 1985). Plasmids pLucTKS3 (driving expression of the firefly luciferase gene) and pRLSRE (driving renilla luciferase gene (Promega) expression) have been previously described (Turkson et al., 2001; Turkson et al., 1999). Cells were grown in Dulbecco's modified Eagle's medium (DMEM) containing 5% iron-supplemented bovine calf serum (BCS), with or without G418.

Cytosolic Extract Preparation and Luciferase Assays.

Cytosolic lysates preparation from fibroblasts for luciferase assays or from baculovirus-infected Sf-9 insect cells have been previously described (Turkson et al., 1998; Turkson et al., 2001; Turkson et al., 1999; Zhang et al., 2000). Luciferase assays were performed as outlined in the supplier's (Promega) manual and measured with a luminometer.

Nuclear Extract Preparation and Gel Shift Assays.

Nuclear extracts were prepared from cell lines and used for EMSA as previously described (Turkson et al., 1998; Yu et al., 1995; Garcia et al., 1997). In some cases, cells were pre-treated with platinum complexes for the indicated times prior to harvesting. Where cells were stimulated with EGF (6 ng/ml), duration of treatment was 15 min. Nuclear extracts were pre-incubated with compounds for 30 min at room temperature prior to incubation with radiolabeled probe. The $^{32}$P-radiolabeled oligonucleotide probes used are hSIE (high affinity sis-inducible element, m67 variant, 5'-AGCTTCATTTCCCGTAAATCCCTA-3') (SEQ ID NO:1) that binds both Stat1 and Stat3 (Garcia et al., 1997;

Wagner et al., 1990), MGFe (mammary gland factor element from the bovine β-casein gene promoter, 5'-AG-ATTTCTAGGAATTCAA-3') (SEQ ID NO:2) that binds Stat1 and Stat5 (Gouilleux et al., 1995; Seidel et al., 1995), the NF-κB binding oligo (5'-TCGACAGAGGGGACTTTC-CGAGAGGC-3') (SEQ ID NO:3), and the oligonucleotide sequence from the DHFR promoter that binds E2F1.

Cell Proliferation and TUNEL Staining.

Proliferating cells were counted by phase-contrast microscopy for viable cells (using trypan blue exclusion. TUNEL staining was carried according to supplier's instructions to detect apoptotic cells. Cells (NIH3T3 or NIH3T3/v-Src) were first treated with or without compounds 24–48 h prior to staining.

Following are examples which illustrate procedures for practicing the invention. These examples should not be construed as limiting. All percentages are by weight and all solvent mixture proportions are by volume unless otherwise noted.

EXAMPLE 1

Inhibition of In Vitro Stat3 DNA-Binding Activity by ISSCPA Complexes

Platinum compounds were evaluated for inhibitory activity against STAT DNA-binding in vitro. Analysis by EMSA of nuclear extracts prepared from epidermal growth factor (EGF)-stimulated fibroblast that activates Stat1, Stat3 and Stat5 shows that preincubation (of extracts of equal total protein) with different concentrations of ISSCPA-1, ISSCPA-3 (also designated herein as CPA-3), or ISSCPA-7 for 30 min prior to incubation with $^{32}$P-labeled oligonucleotide, the m67 high affinity sis-inducible element (hSIE) probe (hSIE binds Stat1 and Stat3) results in dose-dependent reduction in the level of DNA-binding activity of Stat3 and Stat1 (FIG. 1A), with compounds twice more potent against Stat3 over Stat1 ($IC_{50}$ values in the low μmolars shown in Table 1 and Table 2). In contrast similar treatment of nuclear extracts with compounds showed that they have a much reduced inhibitory effect on Stat5 DNA-binding activity (FIG. 1B), suggesting that ISSCPA-1, ISSCPA-3 and ISSCPA-7 preferentially disrupt Stat3 and Stat1 activity.

Figure 1B:
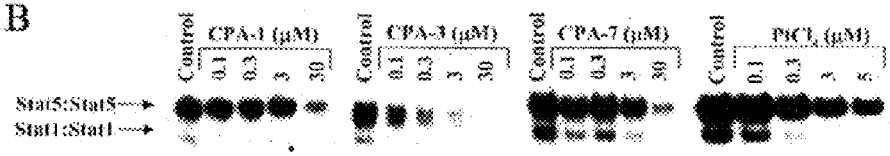
Figure 1C:
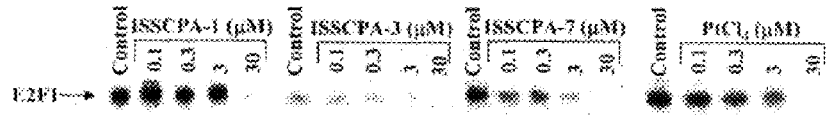
Figure 1D:
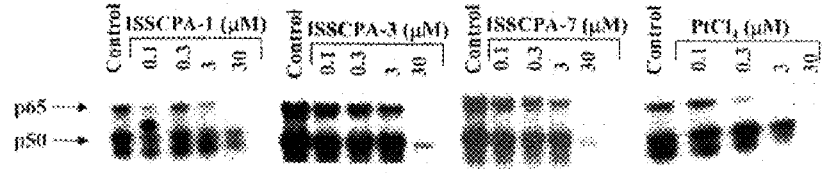

The covalency of platinum in both ISSCPA-1 and ISSCPA-7 is four; thus, whether the observed effects are associated with platinum (IV) was determined. For this purpose, platinum (IV) chloride was evaluated in similar assay. As analyzed by EMSA, results show that pretreatment of nuclear extracts with platinum (IV) chloride disrupts DNA-binding activity of Stat3 similarly as observed for ISSCPA-1 and ISSCPA-7 (FIG. 1A, last 6 lanes). To determine selectivity of compounds for Stat3, effects on other proteins, including E2F1 and NF-κB, were investigated. Analysis by EMSA show that the DNA-binding activities of the two non-STAT related transcription factors are not significantly altered by compounds being evaluated (FIGS. 1C and 1D).

TABLE 1

IC50 values (μM) for disruption of STAT DNA-binding activity in vitro

|  | Stat3:Stat3 | Stat1:Stat3 | Stat1:Stat1 |
| --- | --- | --- | --- |
| ISS CPA-1 | 5 | 9.3 | 20 |
| ISS CPA-3 | 5.8 | 27 | 8.3 |
| ISS CPA-7 | 1.5 | 3.5 | 4.0 |

TABLE 2

IC50 values (μM) for inhibition of cell proliferation

|  | NIH3T3 | NIH3T3v-Src |
| --- | --- | --- |
| ISS CPA-1 | — | 2.3 |
| ISS CPA-3 | — | — |
| ISS CPA-7 | — | 1.3 |

EXAMPLE 2

Platinum Complexes Do Not Modulate Integrity of DNA Sequence

Figure 2:
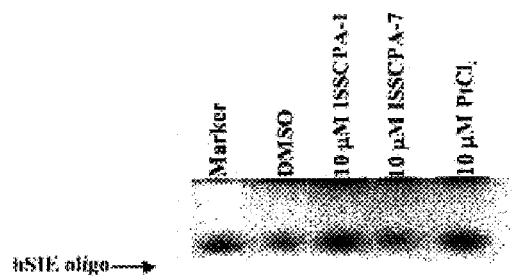
FIG. 2 is a photograph showing agarose gel electrophoresis of DNA treated with or without platinum complexes. Platinum complex-treated hSIE oligonucleotide and DMSO-treated control oligo were heated to 70° C. for 10 min to unwind, re-annealed by cooling overnight to room temperature and analyzed by gel electrophoresis on 2% agarose containing ethidium bromide for UV visualization. Position of band corresponding to hSIE in the gel is shown.

The ability of Cisplatin and analogs thereof to denature DNA sequences by alkylation is known. To determine whether platinum complexes of the invention disrupt DNA integrity, un-annealing and re-annealing studies were performed with cold hSIE oligonucleotide that have been similarly pre-treated with platinum compounds as done in the in vitro DNA-binding assay described in Example 1 and re-annealed oligo was analyzed on a 1.8% agarose gel and bands visualized by staining the gel with ethidium bromide. The oligonucleotide sequence treated with ISSCPA-1, ISSCPA-7 or $PtCl_4$ show an identical migration pattern and band sharpness as the control oligonucleotide that has not been treated with the subject compounds (FIG. 2). This finding indicates that treatment of the hSIE oligonucleotide probe with the subject platinum compounds does not have a denaturing effect, suggesting that the subject platinum compounds may not alter Stat3 binding sequences of the hSIE probe in the in vitro DNA-binding assay.

EXAMPLE 3

Abrogation of Constitutive Stat3 Signaling in Transformed and Tumor Cells by ISSCPA-1 and ISSCPA-7

Figure 3:
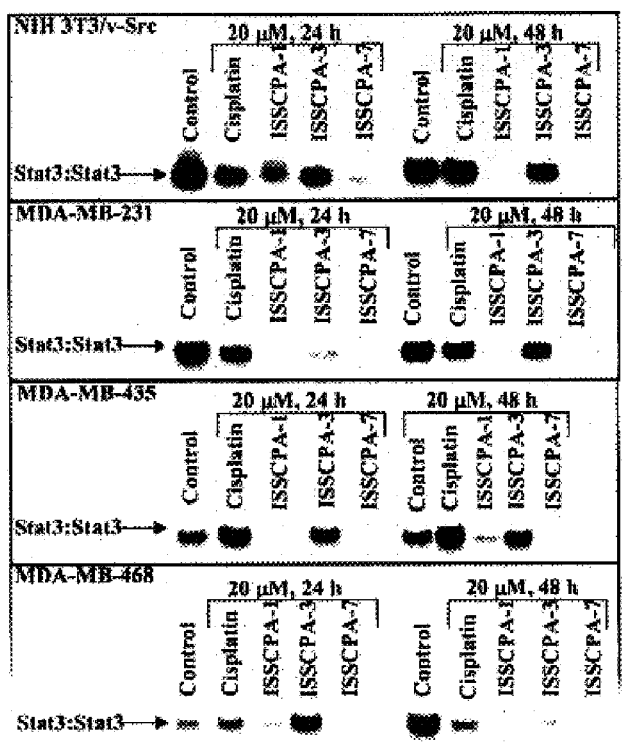
FIG. 3 is a photograph showing the evaluation of effects of platinum complexes on Stat3 activation analyzed by EMSA. Nuclear extracts prepared from malignant cells that contain constitutively-activated Stat3 and treated with platinum complexes for the indicated times were analyzed by EMSA using hSIE oligonucleotide probe. Extracts were prepared from v-Src-transformed NIH3T3/v-Src; human breast carcinoma MDA-MB-231; MDA-MB-435; and MDA-MB-2468. Position of Stat3 DNA complex in gel is shown.
Figures 4A, 4B:
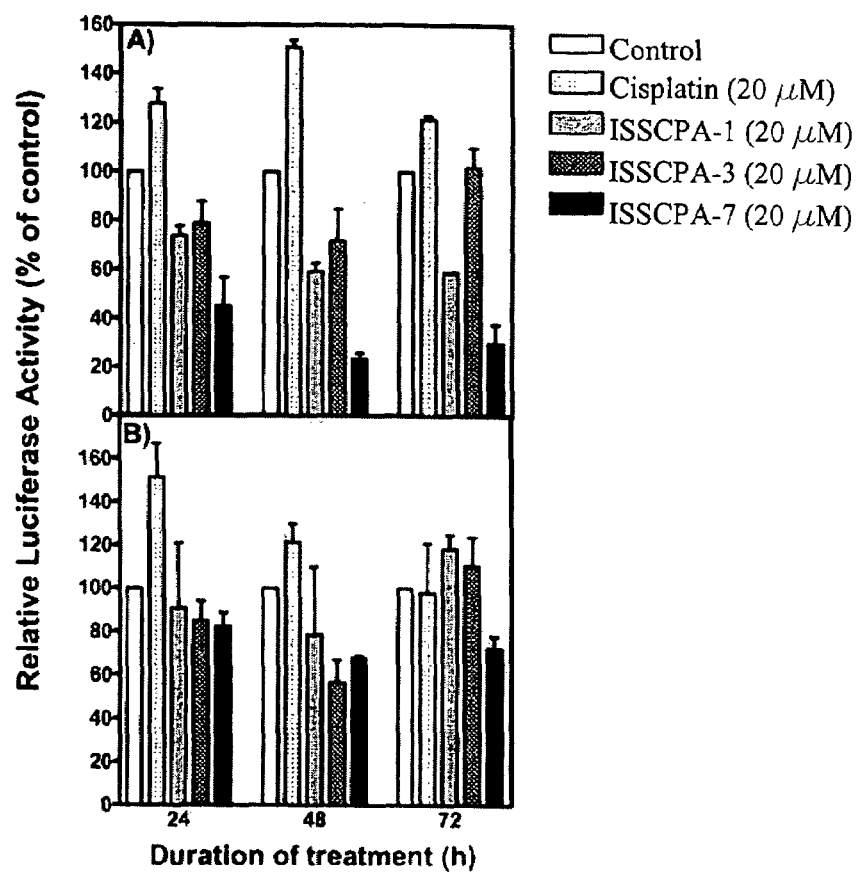
FIGS. 4A–B show inhibition of Stat3-mediated gene expression in intact cells by platinum complexes. v-Src-transformed mouse fibroblasts that stably express Stat3-dependent (NIH3T3/v-Src/pLucTKS3) and Stat3-independent (NIH3T3/v-Src/pRLSRE) luciferase reporters were treated with platinum complexes for the indicated times. Cytosolic extracts were then prepared from cells for Stat3-dependent firefly luciferase activity (FIG. 4A) and Stat3-independent renilla luciferase measurements (FIG. 4B). Values are the means and S.D. of five independent assays.

The effects of platinum complexes on persistent activation of Stat3 in Src-transformed fibroblasts and human tumor cells were investigated. For cells treated with ISSCPA-1 and ISSCPA-7, EMSA analysis of in vitro Stat3 DNA-binding activity in nuclear extracts shows strong inhibition of constitutive Stat3 activation (FIG. 3), suggesting that the compounds block constitutive Stat3 activation. These studies were then extended to evaluate the effects of the platinum complexes on Stat3 transcriptional activity. Both ISSCPA-1 and ISSCPA-7 significantly suppress Stat3-dependent induction of luciferase reporter (FIG. 4), with little or no effect on induction of Stat3-independent luciferase activity (FIG. 4). In contrast, inhibition of constitutive Stat3 activity by platinum complexes ISSCPA-3 and Cisplatin were modest or negligible (FIGS. 3 and 4).

To determine whether platinum complexes of the invention have widespread in vivo effects, changes in other signaling pathways were investigated. The effects of compounds on induction of MAPK, PI-3-kinase and protein kinase C pathways were evaluated. In Src-transformed NIH3T3/v-Src and NIH3T3/hEGFR stimulated with EGF, treatment with platinum complexes of the invention does not alter the levels of tyrosine phosphorylated proteins as analyzed by Western blotting (FIG. 5A). Similarly, induction of MAP kinase Erk1 or Erk2 by EGF was not significantly altered by treatment with compounds (FIG. 5B). These findings together indicate that ISSCPA-1 and ISSCPA-7 are potent inhibitors of constitutive activation of Stat3 in transformed and tumor cells and Stat3-mediated gene expression.

EXAMPLE 4

Inhibition of Cell Growth and Decreased Cell Viability by Platinum Complexes

Figure 6A:
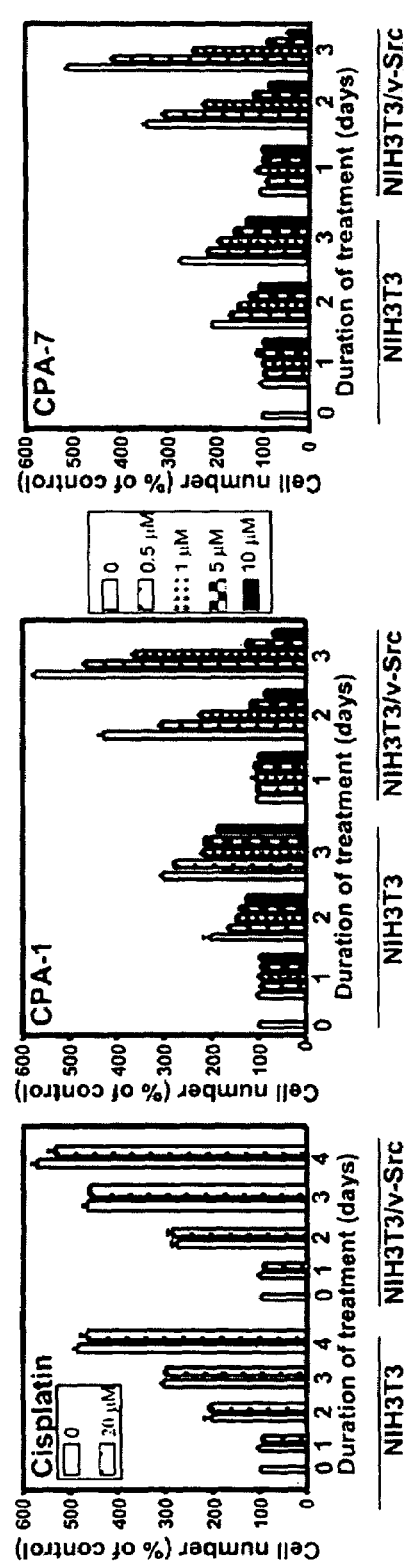
FIGS. 6A and 6B show the effects of platinum complexes on cell proliferation and viability.
Figure 6B:
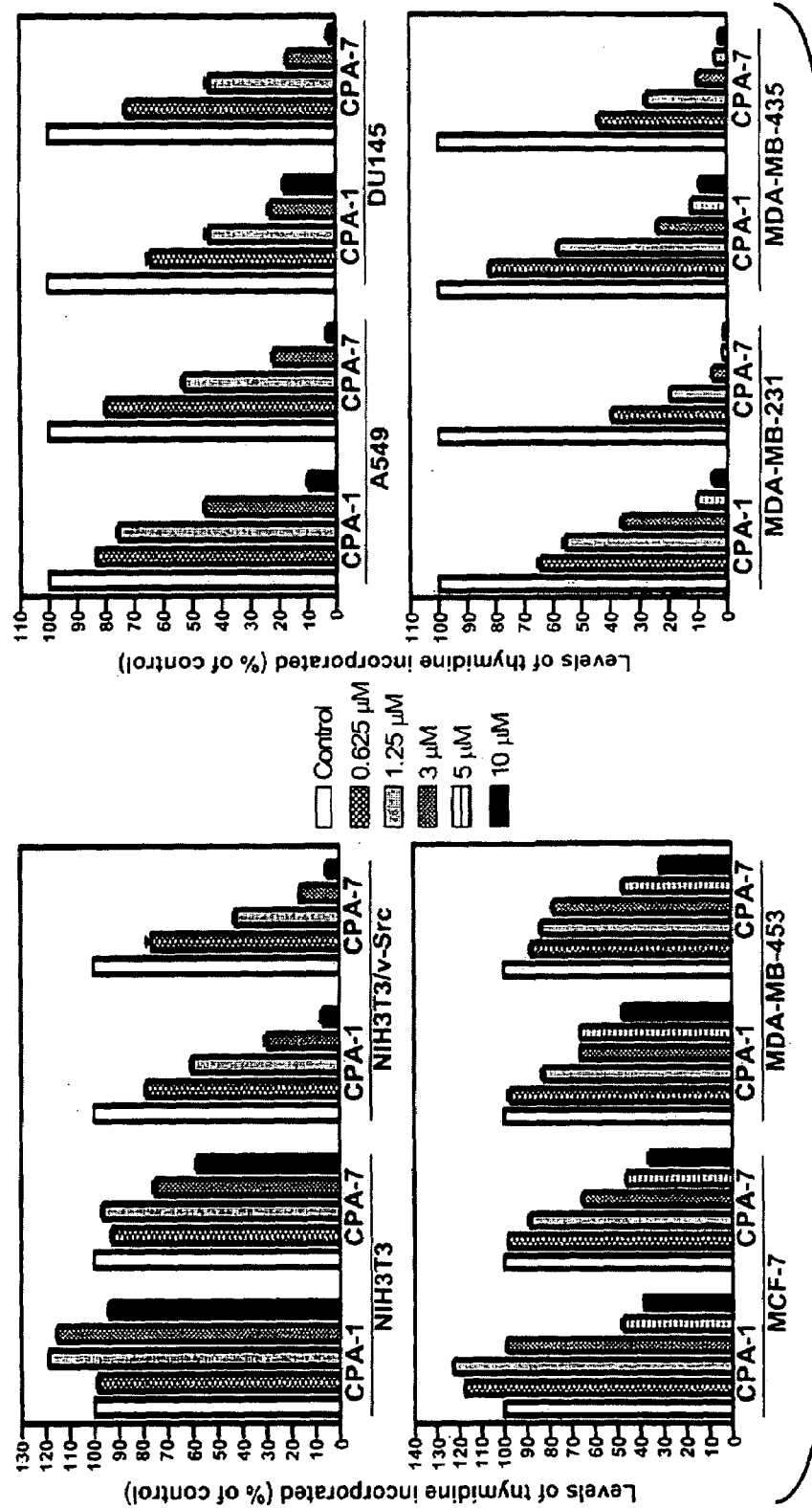

The effects of platinum complexes on cell proliferation measured by [$^3$H]-thymidine incorporation were investigated. Treatment with ISSCPA-1 and ISSCPA-7 strongly inhibited the growth of Src-transformed mouse fibroblasts, as well as of human breast and non-small cell lung cancer cell lines (FIG. 6). In contrast, similar treatment of normal mouse fibroblasts or human tumor cells that do not contain constitutively-active Stat3 only has marginal effect, observed as a reduction in growth rate of treated cells but not growth inhibitory (FIG. 6). Consistent with a key role for Stat3 in cell growth, this data shows that inhibition of constitutively-active Stat3 induces cell growth arrest.

EXAMPLE 5

Induction of Apoptosis by Platinum Compounds

Figure 7:
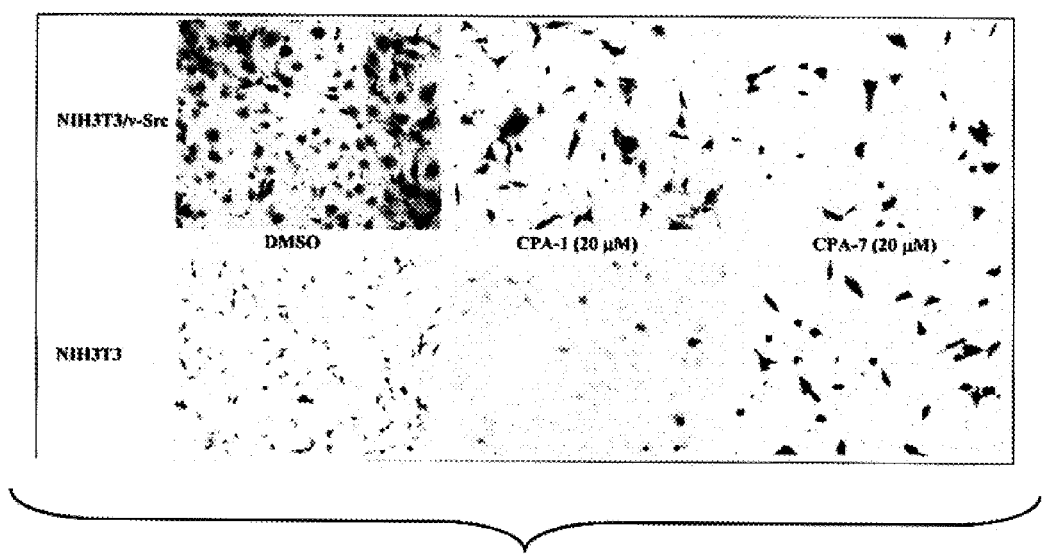
FIG. 7 is a photograph showing induction of apoptosis by platinum complexes. Normal NIH3T3 fibroblasts and their v-Src-transformed counterparts were treated with platinum complexes for 48 h and analyzed for evidence of DNA damage using TUNEL staining kit.

Studies have established a critical role for constitutive Stat3 signaling in the survival of transformed and tumor cells (Catlett-Falcone et al., 1999a; Grandis et al., 2000a; Epling-Burnette et al., 2001; Bowman et al., 2000b; Grandis et al., 2000b; Horiguchi et al., 2002). Effects of the subject platinum compounds on viability and survival of malignant cells were evaluated. To determine whether inhibition of persistently-active Stat3 by the subject compounds results in apoptosis, Src-transformed and normal mouse fibroblasts were treated with the subject platinum compounds and subjected to TUNEL staining for evidence of apoptosis. Results in FIG. 7 show that ISSCPA-1 and ISSCPA-7 induced strong apoptosis in Src-transformed NIH3T3 fibroblasts. In contrast, only a marginal degree of apoptosis was observed in normal fibroblasts that were similarly treated. These results demonstrate that apoptosis is induced in Stat3-dependent transformed cells by platinum complexes of the invention.

EXAMPLE 6

Induction of Regression by Platinum (IV) Chloride of Melanoma and Colon Tumors

The antitumor efficacy of platinum (IV) chloride of the invention using mouse models of melanoma and colon tumors was evaluated. Established tumors were directly injected with doses of platinum (IV) chloride and tumor size subsequently monitored. For both the melanoma and colon tumors, results show complete regression following treatment with platinum (IV) chloride (FIG. 8B), while untreated control tumor continued to grow. In parallel studies, treated tumors were extracted and Stat3 activity determined on the basis of DNA-binding activity analyzed by EMSA. In tumors treated with the platinum (IV) chloride of the invention, constitutively-active Stat3 was strongly attenuated (FIG. 8A). Together, the findings support inhibition of constitutively-active STATs by platinum (IV) chloride leads to regression of melanoma and colon tumors.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Published U.S. Patent Application No. 20030032594
Published U.S. Patent Application No. 20020120100
Published U.S. Patent Application No. 20020035243
Akira, S. (2000) "Roles of STAT3 defined by tissue-specific gene targeting" *Oncogene* 19:2607–2611.
Ardizzoni, A., Antonelli, G., Grossi, F., Tixi, L., Cafferata, M., Rosso, R. (1999) "The combination of etoposide and cisplatin in non-small-cell lung cancer (NSCLC)" *Ann. Oncol.* 10:S13–17.
Bowman, T., Garcia, R., Turkson, J., Jove, R. (2000a) "STATs in oncogenesis" *Oncogene* 19:2474–2488.
Bowman, T., Broome, M., Sinibaldi, N., Wharton, W., Pledger, W. J., Sedivy, J., Irby, R., Yeatman, T., Courneidge, S. A., Jove, R. (2000b) "Stat3-mediated Myc expression is required for Src transformation and PDGF-induced mitogenesis" *Proc Natl. Acad. Sci. USA* 98:7319–7324.
Bromberg, J. F., Horvath, C. M., Wen, Z., Schreiber, R. D., Darnell, J. E., Jr. (1996) "Transcriptionally active Stat1 is required for the antiproliferative effects of both interferon alpha and interferon gamma" *Proc. Natl. Acad. Sci. USA* 93:7673–7678.
Bromberg, J. F., Horvath, C. M., Besser, D., Lathem, W. W., Darnell, J. E., Jr. (1998) "Stat3 activation is required for cellular transformation by v-src" *Mol. Cell. Biol.* 18:2553–2558.
Bromberg, J. F., Wrzeszczynska, M. H., Devgan, G., Zhao, Y., Pestell, R. G., Albanese, C., Darnell, J. E., Jr. (1999) "Stat3 as an oncogene" *Cell* 98:295–303.
Catlett-Falcone, R., Landowski, T. H., Oshiro, M. M., Turkson, J., Levitzki, A., Savino, R., Ciliberto, G., Moscinski, L., Fernandez-Luna, J. L., Nunez, G., Dalton, W. S., Jove, R. (1999a) "Constitutive activation of Stat3 signaling confers resistance to apoptosis in human U266 myeloma cells" *Immunity* 10:105–115.
Catlett-Falcone, R., Dalton, W. S., Jove, R. (1999b) "STAT proteins as novel targets for cancer therapy. Signal transducer an activator of transcription" *Curr. Opin. Oncol.* 11:490–496.
Coffer, P. J., Koenderman, L., de Groot, R. P. (2000) "The role of STATs in myeloid differentiation and leukemia" *Oncogene* 19:2511–2522.
Darnell, J. E., Jr., Kerr, I. M., Stark, G. R. (1994) "Jak-STAT pathways and transcriptional activation in response to IFNs and other extracellular signaling proteins" *Science* 264:1415–1421.
Darnell, J. E., Jr. (1997) "STATs and Gene Regulation" *Science* 277:1630–1635.
Epling-Burnette, P. K., Lui, J. H., Catlette-Falcone, R., Turkson, J., Oshiro, M., Kothapalli, R., Li, Y., Wang, J.-M., Yang-Yen, H.-F., Karras, J., Jove, R., Loughran, T. P., Jr. (2001) "Inhibition of STAT3 signaling leads to apoptosis of leukemic large granular lymphocytes and decreased Mcl-1 expression" *J. Clin. Invest* 107:351–362.
Fukada, T., Hibi, M., Yamanaka, Y., Takahashi-Tezuka, M., Fujitani, Y., Yamaguchi, T., Nakajima, K., Hirano, T. (1996) "Two signals are necessary for cell proliferation induced by a cytokine receptor gp130:involvement of STAT3 in anti-apoptosis" *Immunity* 5:449–460.

Garcia, R., Yu, C. L., Hudnall, A., Catlett, R., Nelson, K. L. Smithgall, T., Fujita, D. J., Ethier, S. P., Jove, R. (1997) "Constitutive activation of Stat3 in fibroblasts transformed by diverse oncoproteins and in breast carcinoma cells" *Cell Growth Diff.* 8:1267–1276.

Garcia, R., Jove, R. (1998) "Activation of STAT transcription factors in oncogenic tyrosine kinase signaling" *J. Biomed. Sci.* 5:79–85.

Garcia, R., Bowman, T. L., Niu, G., Yu, H., Minton, S., Muro-Cacho, C. A., Cox, C. E., Falcone, R., Fairclough, R., Parson, S., Laudano, A., Gazit, A., Levitzki, A., Kraker, A., Jove, R. (2001) "Constitutive activation of Stat3 by the Src and JAK tyrosine kinases participates in growth regulation of human breast carcinoma cells" *Oncogene* 20:2499–2513.

Gouilleux, F., Moritz, D., Humar, M., Moriggl, R., Berchtold, S., Groner, B. (1995) "Prolactin and interleukin-2 receptors in T lymphocytes signal through a MGF-STAT5-like transcription factor" *Endocrinology* 136:5700–5708.

Grandis, J. R., Drenning, S. D., Chakraborty, A., Zhou, M. Y., Zeng, Q., Pitt, A. S., Tweardy, D. J. (1998) "Requirement of Stat3 but not Stat1 activation for epidermal growth factor receptor-mediated cell growth In vitro" *J. Clin. Invest.* 102:1385–1392.

Grandis, J. R., Drenning, S. D., Zeng, Q., Watkins, S. C., Melhem, M. F., Endo, S., Johnson, D. E., Hun, L., He, Y., Kim, J. D. (2000a) "Constitutive activation of Stat3 signaling abrogates apoptosis in squamous cell carcinogenesis in vivo" *Proc. Natl. Acad. Sci. USA* 97:4227–4232.

Grandis, J. R., Zeng, Q., Drenning, S. D. (2000b) "Epidermal growth factor receptor—mediated stat3 signaling blocks apoptosis in head and neck cancer" *Laryngoscope* 110:868–874.

Hirano, T., Ishihara, K., Hibi, M. (2000) "Roles of STAT3 in mediating the cell growth, differentiation and survival signals relayed through the IL-6 family of cytokine receptors" *Oncogene* 19:2548–2556.

Horiguchi, A., Oya, M., Marumo, K., Murai, M. (2002) "STAT3, but not ERKs, mediates the IL-6-induced proliferation of renal cancer cells, ACHN and 769P" *Kidney Int* 61:926–938.

Johnson, P. J., Coussens, P. M., Danko, A. V., Shalloway, D. (1985) "Evaluation of pharmacy and therapeutics committee drug evaluation reports" *Mol. Cell. Biol.* 5:1073–1083.

Kotenko, S. V., Pestka, S. (2000) "Jak-Stat signal transduction pathway through the eyes of cytokine class II receptor complexes" *Oncogene* 19:2557–2565.

Kunisada, K., Tone, E., Fujio, Y., Matsui, H., Yamauchi-Takihara, K., Kishimoto, T. (1998) "Activation of gp130 transduces hypertrophic signals via STAT3 in cardiac myocytes" *Circulation* 98:346–352.

Lin, T. S., Mahajan, S., Frank, D. A. (2000) "STAT signaling in the pathogenesis and treatment of leukemias" *Oncogene* 19:2496–2504.

Nielsen, M., Kaltoft, K., Nordahl, M., Ropke, C., Geisler, C., Mustelin, T., Dobson, P., Svejgaard, A., Odum, N. (1997) "Constitutive activation of a slowly migrating isoform of Stat3 in mycosis fungoides: tyrphostin AG490 inhibits Stat3 activation and growth of mycosis fungoides tumor cell lines" *Proc. Natl. Acad. Sci. USA* 94:6764–6769.

Nielsen, M., Kaestel, C. G., Eriksen, K. W., Woetmann, A., Stokkedal, T., Kaltoft, K., Geisler, C., Ropke, C., Odum, N. (1999) "Inhibition of constitutively activated Stat3 correlates with altered Bcl-2/Bax expression and induction of apoptosis in mycosis fungoides tumor cells" *Leukemia* 13:735–738.

Nitiss, J. L. (2002) "A copper connection to the uptake of platinum anticancer drugs" *Proc. Natl. Acad. Sci. USA* 99:13963–13965.

Persons, D. L., Yazlovitskaya, E. M., Cui, W., Pelling, J. C. (1999) "Cisplatin-induced Activation of Mitogen-activated Protein Kinases in Ovarian Carcinoma Cells: Inhibition of Extracellular Signal-regulated Kinase Activity Increases Sensitivity to Cisplatin" *Clin. Cancer Res.* 5:1007–1014.

Sanchez-Perez, I., Murguia, J. R., Perona, R. (1998) "Cisplatin induces a persistent activation of JNK that is related to cell death" *Oncogene* 16:533–540.

Schindler, C., Darnell, J. E., Jr. (1995) "Transcriptional responses to polypeptide ligands: the JAK-STAT pathway" *Annu. Rev. Biochem.* 64:621–651.

Seidel, H. M., Milocco, L. H., Lamb, P., Darnell, J. E., Jr., Stein, R. B., Rosen, J. (1995) "Spacing of palindromic half sites as a determinant of selective STAT (signal transducers and activators of transcription) DNA binding and transcriptional activity" *Proc. Natl. Acad. Sci. USA* 92:3041–3045.

Smithgall, T. E., Briggs, S. D., Schreiner, S., Lerner, E. C., Cheng, H., Wilson, M. B. (2000) "Control of myeloid differentiation and survival by Stats" *Oncogene* 19:2612–2618.

Song, J. I., Grandis, J. R. (2000) "STAT signaling in head and neck cancer" *Oncogene* 19:2489–2495.

Stark, G. R., Kerr, I. M., Williams, B. R., Silverman, R. H., Schreiber, R. D. (1998) "How cells respond to interferons" *Annu. Rev. Biochem.* 67:227–264.

Turkson, J., Bowman, T., Garcia, R., Caldenhoven, E., de Groot, R. P., Jove, R. (1998) "Stat3 activation by Src induces specific gene regulation and is required for cell transformation" *Mol. Cell. Biol.* 18:2545–2552.

Turkson, J., Bowman, T., Adnane, J., Zhang, Y., Djeu, J. Y., Sekharam, M., Frank, D. A., Holzman, L. B., Wu, J., Sebti, S., Jove, R. (1999) "Requirement for Ras/Rac1-mediated p38 and c-Jun N-terminal kinase signaling in Stat3 transcriptional activity induced by the Src oncoprotein" *Mol. Cell. Biol.* 19:7519–7528.

Turkson, J., Jove, R. (2000) "STAT proteins: novel molecular targets for cancer drug discovery" *Oncogene* 19:6613–6626.

Turkson, J., Ryan, D., Kim, J. S., Zhang, Y., Chen, Z., Haura, E., Laudano, A., Sebti, S., Hamilton, A. D., Jove, R. (2001) "Phosphotyrosyl peptides block Stat3-mediated DNA binding activity, gene regulation, and cell transformation" *J. Biol. Chem.* 276:45443–45455.

Wagner, B. J., Hayes, T. E., Hoban, C. J., Cochran, B. H. (1990) "The SIF binding element confers sis/PDGF inducibility onto the c-fos promoter" *EMBO J.* 9:4477–4484.

Yu, C. L., Meyer, D. J., Campbell, G. S., Lamer, A. C., Carter-Su, C., Schwartz, J., Jove, R. (1995) "Enhanced DNA-binding activity of a Stat3-related protein in cells transformed by the Src oncoprotein" *Science* 269:81–83.

Zhang, Y., Turkson, J., Carter-Su., C. Smithgall, T., Levitzki, A., Kraker, A., Krolewski, J. J., Medveczky, P., Jove, R. (2000) "Activation of Stat3 in v-Src-transformed fibroblasts requires cooperation of Jak1 kinase activity" *J. Biol. Chem.* 275:24935–24944.

We claim:

1. A method for inhibiting a Stat3 transcription factor comprising contacting a tumor cell, cancer cell or transformed cell expressing a Stat3 transcription factor with the platinum complex:

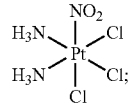

or a pharmaceutically-acceptable salt thereof.

2. The method according to claim 1, wherein said cell is a mammalian cell.

3. The method according to claim 2, wherein said mammalian cell is a human cell, monkey cell, chimpanzee cell, ape cell, dog cell, cat cell, horse cell, cow cell, or pig cell.

4. The method according to claim 1, wherein said platinum complex is encapsulated in a liposome moiety.

* * * * *